(12) United States Patent
Mullani (10) Patent No.: US 7,006,223 B2
(45) Date of Patent: Feb. 28, 2006

(54) DERMOSCOPY EPILUMINESCENCE DEVICE EMPLOYING CROSS AND PARALLEL POLARIZATION

(75) Inventor: Nizar A. Mullani, Sugar Land, TX (US)

(73) Assignee: 3gen, LLC., Dana Point, CA (US)

( * ) Notice: Subject to any disclaimer, the term of this patent is extended or adjusted under 35 U.S.C. 154(b) by 200 days.

(21) Appl. No.: 10/384,110

(22) Filed: Mar. 7, 2003

(65) Prior Publication Data

US 2004/0174525 A1    Sep. 9, 2004

(51) Int. Cl.
*G01J 4/00* (2006.01)
(52) U.S. Cl. ............................ 356/369; 600/476; 606/9
(58) Field of Classification Search ........ 356/364–369, 356/445–448, 39; 600/410, 425, 476–478; 606/3, 10, 16, 9; 250/461.1, 461.2, 459.1
See application file for complete search history.

(56) References Cited

U.S. PATENT DOCUMENTS

| | | | |
|---|---|---|---|
| 2,120,365 A | 6/1938 | Kriebel | |
| 2,866,375 A | 12/1958 | Wells et al. | |
| 2,947,212 A | 8/1960 | Woods | |
| 3,062,087 A | 11/1962 | Zandman et al. | |
| 4,007,979 A | 2/1977 | Coblitz | |
| 4,398,541 A | 8/1983 | Pugliese | |
| 4,773,097 A * | 9/1988 | Suzaki et al. | 382/128 |
| 4,846,184 A | 7/1989 | Comment et al. | |
| 4,957,368 A | 9/1990 | Smith | |
| 4,998,818 A | 3/1991 | Kugler et al. | |
| 5,146,923 A * | 9/1992 | Dhawan | 600/476 |
| 5,198,875 A | 3/1993 | Bazin et al. | |
| 5,343,536 A | 8/1994 | Groh | |
| 5,363,854 A * | 11/1994 | Martens et al. | 600/477 |
| 5,690,417 A | 11/1997 | Polidor et al. | 362/244 |
| 5,742,392 A | 4/1998 | Anderson et al. | |

(Continued)

FOREIGN PATENT DOCUMENTS

IT    01300568    10/1999

OTHER PUBLICATIONS

"Comparison of OPS imaging and conventional capillary microscopy to study the human microcirculation," p. 74-78. Keshen R. Mathura et al, the American Physiological Society, 2001.

(Continued)

*Primary Examiner*—Hoa Q. Pham
(74) *Attorney, Agent, or Firm*—Stetina Brunda Garred & Brucker (57) ABSTRACT

The present invention is a hand held dermoscopy epiluminescense device with a magnification lens and an associated ring of luminous diodes powered by an on board battery. Every other diode in the ring operates as first and second light sources. The even diodes are filtered by a first polarization ring and the odd diodes are filtered by a second polarization ring. Each polarization ring has an open center for the lens and openings sized and positioned to correspond to the even or odd diodes to only filter one set. A viewing polarizer is provided and is cross-polarized relative to the first polarization ring and is parallel-polarized with the second polarization ring. A three way switch which provides on demand cross-polarized, parallel-polarized and a combination thereof for epiluminescence. A second embodiment provides even diodes of a first color and odd diodes of a second color. A third embodiment employs the alternating colored diodes of the second embodiment as well as the cross and parallel polarization of the light from the diodes as found in the first embodiment.

20 Claims, 6 Drawing Sheets

U.S. PATENT DOCUMENTS

| | | | | |
|---|---|---|---|---|
| 6,032,071 | A | | 2/2000 | Binder ........................ 600/476 |
| 6,069,565 | A | * | 5/2000 | Stern et al. .................. 340/583 |
| 6,081,612 | A | * | 6/2000 | Gutkowicz-Krusin et al. .......................... 382/128 |
| 6,207,136 | B1 | | 3/2001 | Matsuoka |
| 6,384,988 | B1 | | 5/2002 | Müller et al. ................ 359/798 |
| 6,483,247 | B1 | | 11/2002 | Edwards et al. |
| 6,587,711 | B1 | | 7/2003 | Alfano et al. |
| 2003/0026110 | A1 | * | 2/2003 | Satoh et al. ................. 362/572 |
| 2003/0045799 | A1 | * | 3/2003 | Bazin et al. ................ 600/476 |

OTHER PUBLICATIONS (Brochure) 3gen, LLC., "First in Pocket Epiluminescence Microscopy," 1 page, Mar. 5, 2001 (Estimated publication date).

(Brochure) 3gen, LLC., "3gen the Beauty of Revolutionary Innvation," 3 pages (trifold), Feb. 15, 2002 (Estimated publication date).

(Internet literature) www.syrisscientific.com, "Technical," 1 page,(Unknown publication date).

* cited by examiner

DERMOSCOPY EPILUMINESCENCE DEVICE EMPLOYING CROSS AND PARALLEL POLARIZATION

CROSS-REFERENCE TO RELATED APPLICATIONS (Not Applicable)

STATEMENT RE: FEDERALLY SPONSORED RESEARCH/DEVELOPMENT (Not Applicable)

FIELD OF THE INVENTION

The present invention relates generally to an epiluminescence device used in dermoscopy. More particularly, the invention comprises an improved apparatus for illuminating the skin for medical examination by providing cross-polarized and parallel-polarized light to aid in viewing internal structures as well as the skin surface.

BACKGROUND OF THE INVENTION

Dermoscopy is the term used to describe methods of imaging skin lesions. Skin is the largest organ in the body and it is the most easily accessible organ for external optical imaging. For early detection of cancers, it is important that the skin be medically examined for lesions.

With over forty (40%) percent of the cancers occurring on the skin (American Cancer Society Statistics 2001, Perelman 1995), and incidence of skin cancer increasing each year, tools and methods of imaging skin lesions are becoming increasingly important. Most of the cancers detected on the skin are Basal Cell Carcinoma (BCC) and Squamous Cell Carcinoma (SSC), which are differentiated from melanoma, a more deadly form of skin cancer. The early detection of skin cancer allows for inexpensive treatment before the cancer causes more severe medical conditions. Thus, there is a great need in the art for simple inexpensive instruments that allow for the early screening for skin cancer.

Because skin is partially translucent, dermoscopy utilizes tools for visualization of the pigmentation of the skin below the surface. In this regard, when attempting to visualize the deeper structure of the skin, it is important to reduce the reflection of light from the skin which may obscure the underlying structures. Methods used to reduce the surface reflection from the skin are referred to as epiluminescence imaging. There are three known methods for epiluminescence imaging of the skin, oil-immersion, cross-polarization, and side-transillumination. Oil-immersion and cross-polarization methods have been extensively validated for early skin cancer detection while side transillumination methods are currently undergoing study and clinical validation.

Oil-immersion devices are generally referred to as Dermatoscopes. Dermatoscopes permit increased visualization of sub surface pigmentation by using a magnification device in association with a light source. In operation, oil is placed between the skin and a glass faceplate. The placement of oil and a glass interface between the eye and the surface of the skin reduces the reflected light from the skin, resulting in deeper visualization of the underlying skin structure.

While oil-immersion has proved to be an excellent method of epiluminescence imaging of the skin, demonstrating improved sensitivity for melanoma detection, it is messy and time consuming for the physician. As a result, the Dermatoscope is used mostly by physicians that specialize in pigmented lesions and for evaluation of suspicious lesions that cannot be diagnosed visually. Also, the oil-immersion of the Dermatoscope has been found to be less effective for BCC and SCC imaging. The pressure created by the compression of the glass faceplate causes blanching of blood vessels in the skin resulting in reduced capability of the Dermatoscope for imaging the telangiectesia that is often associated with BCC or other malignant lesions.

Cross-polarization or orthogonal polarization is another method of reducing the reflection of the light from the surface of the skin to aid in the medical examination of the skin. Light emanating from a light source is first linearly polarized, so that the orientation of the light falling on the skin surface is in the same plane of polarization. As the light enters the skin, its polarization angle changes such that the light is reflected from a deeper structure. However, the light reflected from the surface of the skin is still polarized in the same plane as the incident light. By including a second polarizer in the path of the reflected light from the skin, a selective filtering of light can be achieved.

Most of the light directed to the skin's surface is reflected as the refractive index of skin is higher than that of air. The reflection of light, off of the skin, is analogous to the reflection of light off of the surface of water. Accordingly, the information received by the eye carries mostly information about the contour of the skin surface rather than the deeper structures. Remaining light enters the skin and is absorbed or is reflected back in a scattered fashion. By polarizing the incident light with a second of polarizer, the specular component of the reflected light is blocked by the viewing polarizer, thus producing an enhanced view below the skin surface. Accordingly, inflammation, color, pigmentation, hair follicles and blood vessels may be viewed.

When the incident light and the second polarizer are parallel, the surface topography and properties of the skin are highlighted and enhanced. In this regard, if the polarizer in the path of the light from the skin to the eye is polarized in the same orientation of the incident light, only the light from its polarization angle will be allowed to pass through the lens. Cross-polarization imaging of the body was originally described by R. R. Anderson ("Polarized light examination and photography of the skin." Archives Dermatology 1991; 127; 1000–1005). Later, Binder introduced the MoleMax manufactured by Derma Instruments (Vienna, Austria) for the examination and mapping of pigmented lesions. Binder further developed the no-oil cross-polarization epiluminescence method. MoleMax, however, while validating clinically the improved diagnosis and accuracy without the use of oil, still used a glass faceplate and video imaging system to execute skin examinations.

In light of many of the difficulties associated with prior dermoscopy systems, a simple and cost-effective diagnostic systems remained unavailable for general dermatologists to use on a routine clinical basis. Dermoscopy, until recently, remained generally a research tool utilized in special clinical cases.

More recently, however, a substantial advancement in skin cancer detection occurred through a simple device identified as DermLite®, manufactured and marketed by 3Gen, LLC. of Monarch Beach, Calif. With this low cost and easy to use DermLite® Device, screening for cancer by dermatologists in routine clinical examination of skin disease has become a reality. The DermLite® device uses cross-polarization epiluminescence imaging through use of white light emitting diodes (LEDs), a high magnification lens (10×), and a lithium ion battery contained in a small lightweight device.

In the DermLite® device, a window is incorporated into a compact housing, and a plurality of white light LEDs encircle a magnifying lens. The DermLite® device incorporates cross-polarization filters that reduce the reflection of light from the surface of the skin and permits visualization of the deeper skin structures. Light from eight (8) LEDs is polarized linearly by a polarizer, which is annular in shape and located in front of the LEDs. The imaging viewed through the magnifying lens is also linearly polarized by using a polarizer that is located in front of the lens. The LEDs have a narrow beam angle that concentrates the light into a small area, pointing the incident light to the center to increase the brightness of the area being viewed. Thus, light from the LEDs passes through the polarizer which enters the skin and reflects back through the viewing polarizer to create cross-polarization allowing examination to look deeper within the skin structure. Although, the DermLite® product has been recognized as a major advancement in the art of routing clinical diagnosis and analysis of skin cancer lesions, DermLite® device does not provide a mechanism for enabling the user to additionally view parallel-polarized light, or a combination of cross-polarized light and parallel-polarized light.

The DermLite® Platinum® product, also manufactured by 3Gen, LLC. was developed to provide variable polarization. Variable polarization is achieved by a rotating dial. Rotation of the polarizer to a cross-polarization cancels out the surface reflection for an in-depth look at the deeper pigmentation in lesion structure. Rotation to parallel polarization allows a clear view of the skin surface. The DermLite® Platinum® product requires manual manipulation of the dial which may cause user to lose the viewing spot, or otherwise interfere with examination. Further, DermLite Platinum® does not provide a user the ability to view the skin with an instantaneous switch over from cross-polarization to parallel polarization.

Recent discoveries in optical fluorescence imaging have identified several molecules having fluorescence properties that are useful in medicine. In dermatology, simple applications such as delta-aminolaevulinic acid (ALA) applied topically have been found to enhance the visualization of basal cell cancer from normal tissue, when illuminated with UV/Blue light. Fluorescein is another fluorescent compound that has been in clinical use in opthamology for several years and has great potential for use in dermatological applications. Indocyanine green (ICG), Methylene Blue, and ethyl nile blue are contrast agents that are used to increase light absorption in blood vessels. There are several FDA approved optical fluorescence tracers already approved for clinical use, and several more new probes may be applicable in the future. However, the use of fluorescence imaging of the skin has been illusive for clinical dermatologist because of the complexity and costs of the associated equipment.

In current applications, such as in the application of ALA topically to a basal cell carcinoma to a BCC, conventional white light visual images of the BCC are displayed next to the fluorescence excited images of ALA in the BCC. The ALA is taken up by the active areas of cancer, converted to porphyrin IX, and fluoresces when exposed to UV/Blue light. It becomes apparent that the fluorescent areas of the BCC may not coincide with the anatomical features of the BCC as shown in white light. Currently the side-by-side comparison is only available by taking two separate images and co-registering these images later in the computer.

Thus, there is a great need in the art for a device that will allow clinical viewing of skin lesions which provides on demand switching from cross-polarized imaging to parallel-polarized imaging and a combination of both. Further there is a great need in the art for a clinical viewing of skin lesions that can toggle back and forth from a white light to a colored or UV light in order to contrast and compare images.

BRIEF SUMMARY OF THE INVENTION

The present invention relates to a dermoscopy epiluminescence device used in the medical diagnosis of skin lesions. The device is a hand held modular housing incorporating a magnification lens and associated lighting scheme for examining the epidermis on humans. The light sources of the lighting scheme are powered by an on board lithium battery and are controlled by a three way switch which provides on demand cross-polarized, parallel-polarized and a combination thereof for epiluminescence.

More particularly, a first embodiment of the present invention comprises a generally circular optical lens incorporated into the housing of the device. The lens produces a magnified image of the skin to be observed by a viewer. In the first embodiment the lens is a 15 mm diameter Hastings lens with a 10× optical gain. The viewer observes the magnified skin through the lens window of the housing. The viewing is aided by a plurality of luminous diodes positioned within the housing and about the circumference of the lens. The diodes direct light upon the skin to be viewed. The LEDs are white high light output Indium Gallium Nitride LEDs. Two light circuits form first and second illumination sources forming a ring of alternating diodes about the lens. A switch is provided that when not in operation has a normal OFF mode. In operation the switch has a first ON mode for initiating the first illumination source (i.e. every other diode on the first light circuit), a second ON mode for initiating the second illumination source (i.e. every other diode on the second light circuit) and a third ON mode for initiating both said first and second illumination sources simultaneously (i.e. all diodes).

A first polarizer filter comprises a planar annular ring defining a generally circular center opening and an outer ring. The center opening of the annular ring of the first polarizer is positioned in alignment with the circular optical lens to provide an unobstructed view of the skin through the lens and the housing. The outer ring of the first polarizer includes a plurality of openings sized and positioned to correspond to the diodes of the second illumination source (i.e. every other diode of the second light circuit) such that light emitted from the diodes of the second illumination source passes through the openings unfiltered by the first polarizer. Because there are no corresponding openings for the diodes of the first illumination source (i.e. every other diode on the first light circuit) light emitted from first source diodes is polarized by the outer ring of the first polarizer filter.

A second polarizer filter comprises a planar annular ring defining a generally circular center opening and an outer ring. The center opening of said annular ring of the second polarizer is positioned in alignment with the circular optical lens to provide an unobstructed view of the skin through the lens and housing. The second polarizer is 90 degrees out of phase with the first polarizer. The outer ring of the second polarizer has a plurality of openings sized and positioned to correspond to the diodes of the first illumination source (i.e. every other diode on the first light circuit) such that light emitted from the diodes of the first illumination source passes through the openings unfiltered by the second polarizer. Because there are no corresponding openings for the diodes of the second illumination source (i.e. every other diode on the second light circuit) light emitted from second source diodes is polarized by the outer ring of the second polarizer filter.

A viewing polarizer is also provided positioned in the housing in line with viewing corridor of the optical lens. The viewing polarizer filters light reflected back from the skin and is cross-polarized relative to said first polarizer and is parallel-polarized relative to said second illumination source. The cross-polarization aids the examiner in viewing deeper structures of the skin while the parallel polarization aids in viewing the topography of the skin.

In a second embodiment of the invention, the ring of diodes that surround the lens incorporate alternating light wavelengths of differing colors. In operation, a user initiates the first light circuit by operating the first ON mode of the housing switch to light every other diode of a first color. The user then can initiate the second ON mode to light every other diode of a second color. Finally the user can initiate a third ON mode and light both sets of diodes to emit both colors simultaneously. For example, one set of lights could be white light LEDs and the second set of light can be a UV/Blue LEDs. Fluorescence imaging provides functional information about the disease, while the standard white light epiluminescence imaging provides the anatomical information that the physician is familiar with in viewing skin disease. Combining the UV/Blue light image with the standard white light image, into a device that is simple and easy to use can be achieved by using a "flicker" method of image integration in the eye, whereby two sets of images are presented one after the other. Switching back and forth between the two sets of images allows the brain to "co-register" the two different images without the need for computers. A third embodiment employs the alternating colored diodes of the second embodiment as well as the cross and parallel polarization of the light from the diodes as found in the first embodiment.

BRIEF DESCRIPTION OF THE DRAWINGS

These as well as other features of the present invention will become more apparent upon reference to the drawings wherein.

DETAILED DESCRIPTION OF THE INVENTION

The detailed description as set forth below in connection with the appended drawings is intended as a description of the presently preferred embodiments of the present invention, and does not represent the only embodiment of the present invention. It is understood that various modifications to the invention may be comprised by different embodiments and are also encompassed within the spirit and scope of the present invention.

Figure 1:
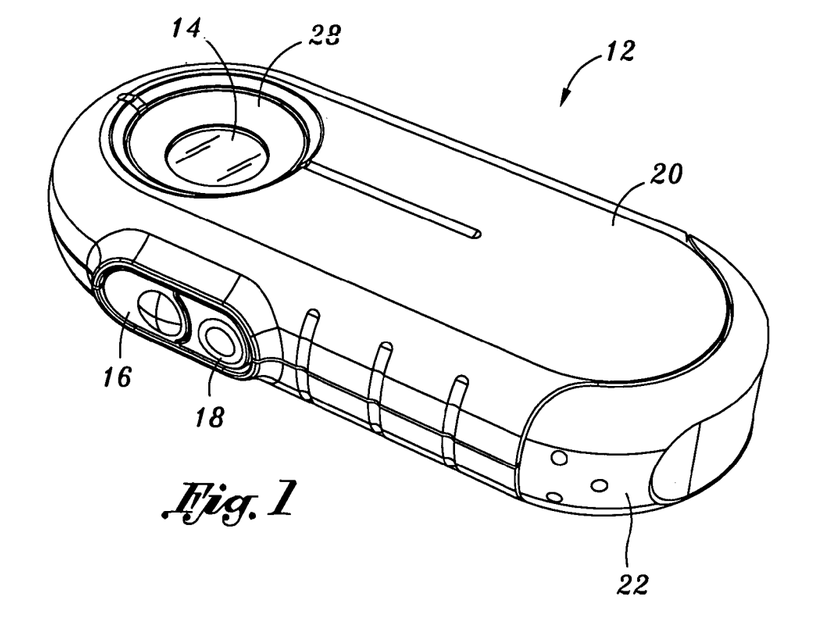
FIG. 1 is a is a top perspective view of the device of the present invention.
Figure 2:
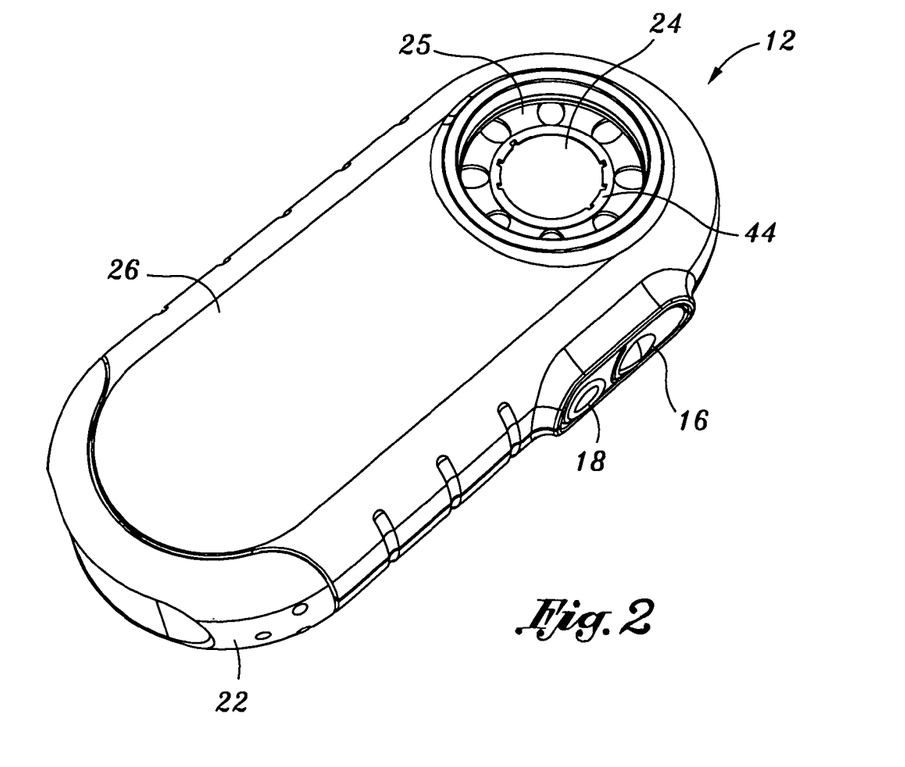
FIG. 2 is a bottom perspective view of the device of the present invention.

Referring particularly to FIGS. 1 and 2, there are shown a top and bottom perspective views, respectively, of the dermoscopy epiluminescence device 12 of the present invention. The device 12 is lightweight and compact, and can easily fit within the shirt pocket of a user. The outer structure of the device 12 can be utilized in association with the first embodiment (FIGS. 3–5), the second embodiment (FIG. 6) and third embodiment (FIG. 7). The exterior appearance of the device for each of the first, second and third embodiments would be identical as shown in FIGS. 1 and 2.

FIG. 1 shows the top perspective view of the device 12 showing the viewing port of the lens 14 incorporated into a housing 20. A battery cover 22 may be removeably secured to the housing 20 to provide access to an interior compartment for insertion and removal of a battery.

Also shown is a switch 16 for initiating a first light source and a switch 18 for initiating the second light source.

Referring particularly to FIG. 2, a bottom perspective view of the device 12 is shown. A light portal is incorporated into the housing 20 to expose a viewing polarizer 24. A plurality of diodes (not shown) encircle the viewing polarizer within the housing 20 and direct light though a multiple layer filter ring 25. Light from the diodes (not shown) is directed onto the skin surface to aid lighting the magnified area to be viewed.

Figure 3:
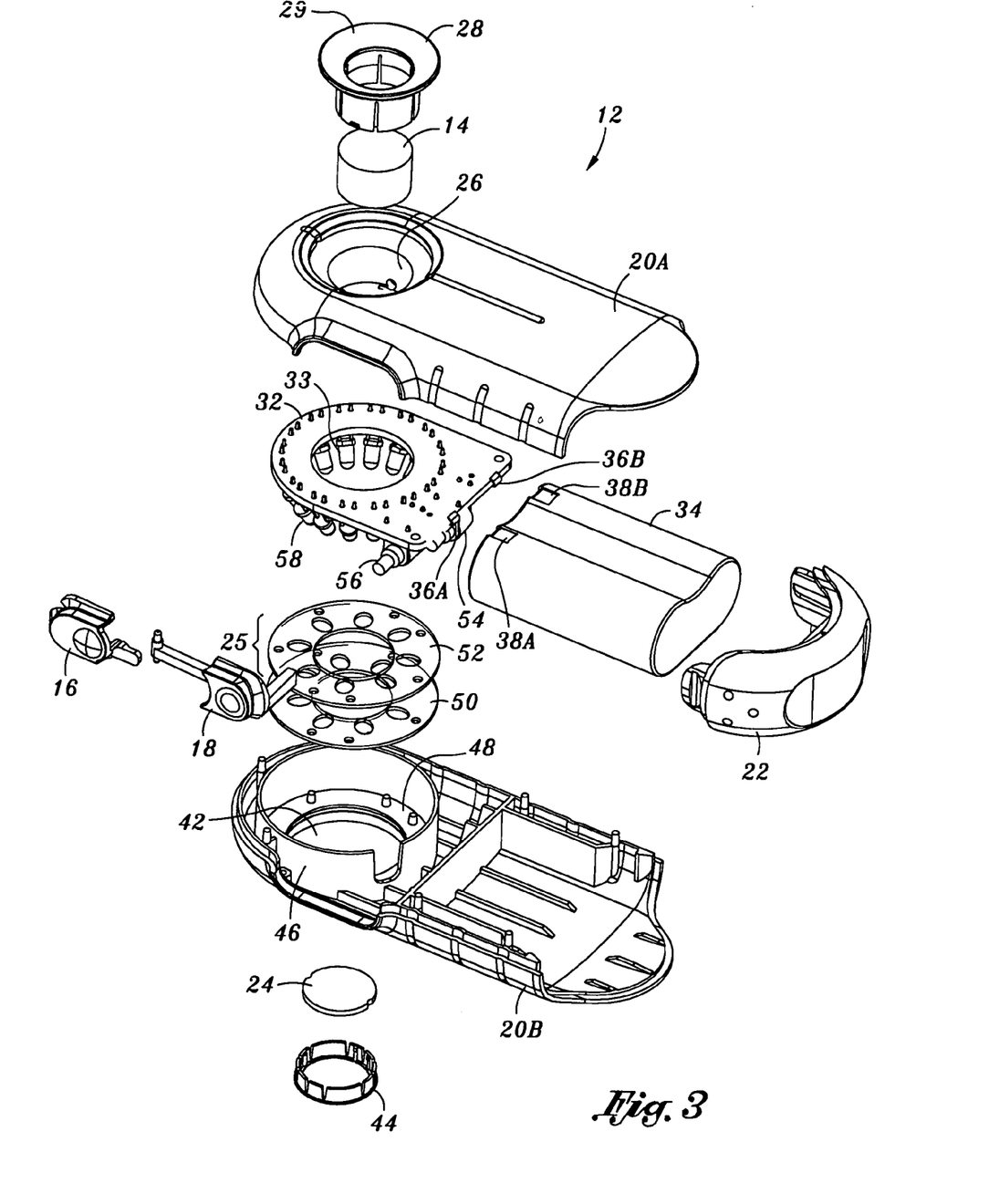
FIG. 3 is an exploded top view of a first embodiment of the present invention.
Figure 4:
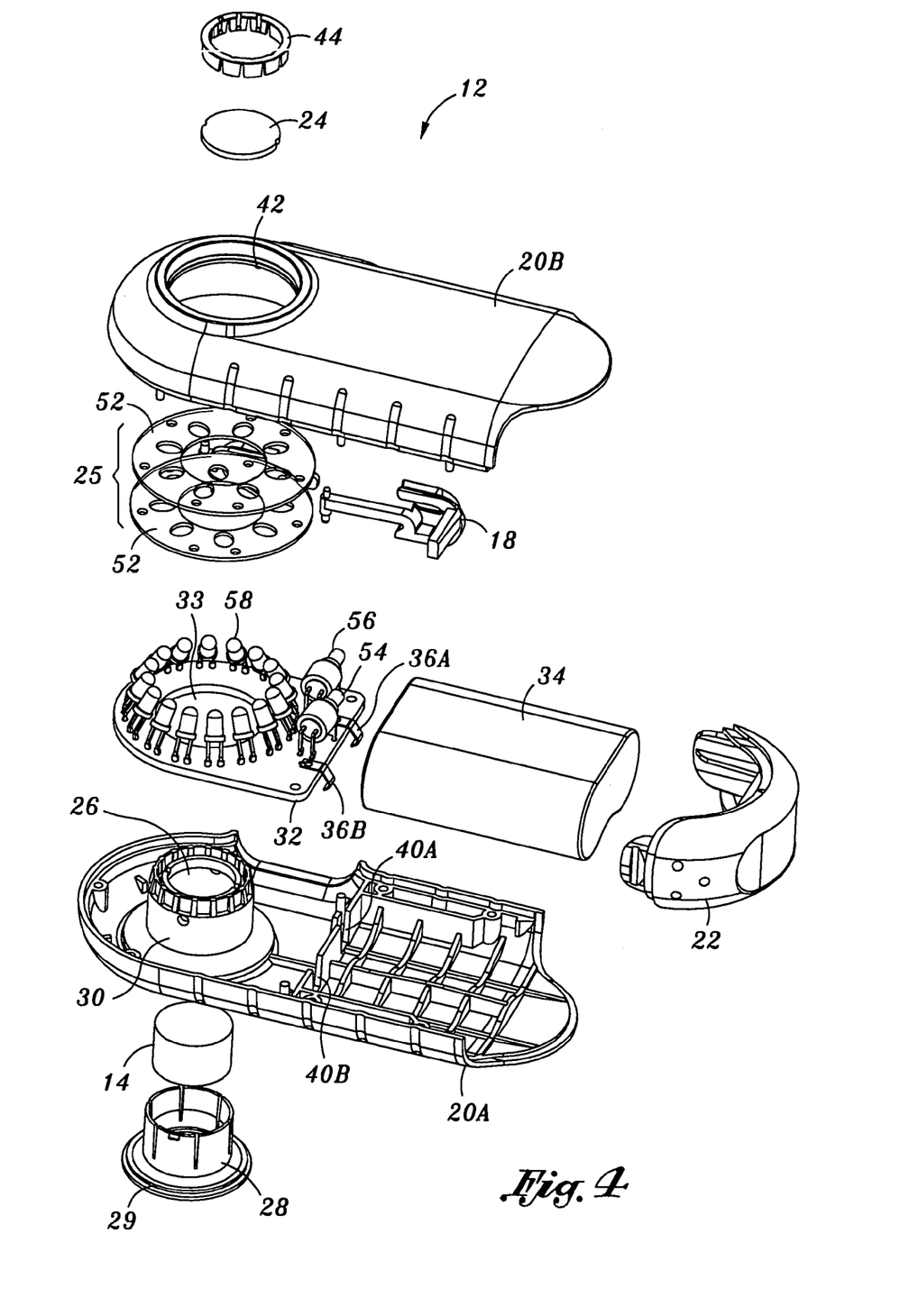
FIG. 4 is and exploded bottom view of a first embodiment of the present invention.

Referring particularly to FIGS. 3 and 4, there is shown a first embodiment of the present invention. FIG. 3 is an exploded top view of the device 12 and FIG. 4 is an exploded bottom view of the device 12. The housing 20 includes top component 20a and bottom component 20b. The top component 20a, bottom component 20b and battery cover 22 are formed from molded lightweight durable plastic. The plastic is a PVC derivative material and may be formed from acrylic or lexan. Additionally, the housing may be formed from metal such as aluminum. Components 20a, 20b and cover 22 are interconnected to form the outer housing 20 as shown in FIGS. 1 and 2.

The top housing component 20a includes an aperture 26 for receiving the combination of the optical lens 14 inserted within the lens sleeve 28. Shown best in FIG. 4, the underside of the top housing component 20a is shown wherein the aperture 26 incorporates a downwardly protruding collar for receiving the lens 14 within the lens sleeve 28. The lens sleeve 28 incorporates an annular lip 29 which engages the sloped sides of the aperture 26 to complete the exterior of the viewing port of the housing 20. The lens sleeve 28 operates to securely hold the lens 14 in place within the aperture 26. The lens 14 in the first embodiment is preferably a 15 mm diameter Hastings lens with a 10× optical gain. Although the first embodiment employs a Hastings lens, the lens may be a single convex lens, a combination of two or more lenses, a double achromat lens, or a combination of double achromat lenses. In addition, the lens may incorporate aspherical lenses to accommodate better optics and lower distortion. The lenses coated with an antireflection coating may be used and may additionally include a color filter to selectively filter light passing through the lens.

Although the invention shows a hand held unit without imaging equipment attached, it is contemplated by the present invention that the same could be used with a camera, and that the size and shape of the lens would be modified to accommodate the same.

The protruding collar 30 is part of the unitary structure of the upper housing component 20a. The cylinder 30 protrudes through the interior components of the housing 20, including a printed circuit board (PCB) 32 having an opening 33 to extend to the light portal of bottom component 20b. A battery 34 nests within a battery chamber formed by the top component 20a and bottom component 20b. PCB 32 includes electrical contacts 36a and 36b for interfacing with the battery 34 contacts 38a and 38b. The upper housing 20a includes slots 40a and 40b to allow the PCB contacts 36a and 36b to protrude from the circuit board 32 into the battery chamber and contact the battery leads 38a and 38b. In all embodiments of the present invention, the battery 34 is an extended charge lithium battery, however, it is understood and contemplated by the present invention that the battery could be any suitable battery package such as a one-time lithium battery or rechargeable lithium battery. The invention additionally contemplates use of a DC power supply that may have a suitable DC output to drive the LEDs.

The bottom component 20b includes a viewing aperture 42. The viewing polarizer 24 and sleeve 44 cap off the opening of the collar 30. Viewing polarizer 24 is composed of acrylic plastic with polarization material embedded within the polarizer. It is contemplated by the invention that the viewing polarizer 24 may be constructed of glass, also with material embedded or coated on the glass. In addition, the viewing polarizer 24 may be coated with a filter material that can selectively filter out some of the light frequencies emanating from the object. Alternatively, the secondary filter assembly made of plastic or glass with the capability of filtering the light may be placed in the path of the viewing lens to filter out some of the light. Bottom housing component 20b includes a bottom collar 46 formed therein. A lip 48 incorporating a plurality of guide tabs, is formed between the collar 46 and the aperture 42. The lip 48 and guide tabs are adapted to engage bottom annular polarizer 50 and a top annular polarizer 52. The top 52 and bottom 50 polarizers are 90 degrees out of phase. The bottom 50 polarizer is in cross polarization with the viewing polarizer 24 and top polarizer 52 is in parallel polarization with the viewing polarizer 24. The top 52 and bottom 50 polarizers are composed of acrylic plastic and include polarization at different angles. The polarizers 50 and 52 may also be coated with a special material to filter out some of the light emanating from the LEDs, or alternatively the annular polarizer 50 and 52 may be sandwiched with a color filter acrylic material. The aperture 42 is wide enough to permit a viewing corridor from the lens sleeve 28 through the housing 20 to the aperture 42 while allowing portions of the top 52 and bottom 50 polarizers to be exposed and to filter light emitting diodes inside the housing 20.

Sixteen light emitting diodes 58 ring the circuit board. The diodes are preferably white high light output Indium Gallium Nitride LEDs, however any suitable lighting diodes are appropriate. The even diodes are on a single circuit and the odd diodes are an a separate single circuit. In the shown embodiment, the LEDs 58 are a standard white LED made with phosphorescence phosphors to create white light. It is additionally contemplated by the present invention that tri-colored LEDs, with individual red, green and blue LEDs that can combine form white light may be utilized. It is contemplated by the present invention that the LEDs may have focusing lenses to concentrate the light into a smaller and tighter beam. The LEDs may additionally be comprised of indium gallium arsenide material, or any other like semiconductor material. The PCB board 42 incorporates switch contacts 54 and 56. The polarizing parallel switch 16 engages switch contact 56 and the parallel-polarizing switch 18 engages with contact 54. Thus, engaging switch 16 initiates a first light source, which are the eight even diodes 58 and the switch 18 initiates the second light source, which are the other eight odd diodes. Both switches 56 and 54 may be operated simultaneously to light all sixteen diodes 58 simultaneously. It is contemplated by the present invention that the device may employ three or more switches operative to initiate three or more sets of diodes.

A first polarizer filter 50 comprises a planar annular ring defining a generally circular center opening and an outer ring. The center opening of the annular ring of the first polarizer 50 is positioned in alignment with the circular optical lens 14 to provide an unobstructed view of the skin through the lens 14 and the housing 20. The outer ring of the first polarizer 50 includes a plurality of openings sized and positioned to correspond to the diodes 58 of the second illumination source (i.e. every other diode 58 of the second light circuit) such that light emitted from the diodes 58 of the second illumination source passes through the openings unfiltered by the first polarizer 50. Because there are no corresponding openings for the diodes of the first illumination source (i.e. every other diode on the first light circuit) light emitted from first source diodes is polarized by the outer ring of the first polarizer filter 50.

A second polarizer filter 52 comprises a planar annular ring defining a generally circular center opening and an outer ring. The center opening of said annular ring of the second polarizer 52 is positioned in alignment with the circular optical lens 14 to provide an unobstructed view of the skin through the lens 14 and housing 20. The second polarizer 52 is 90 degrees out of phase with the first polarizer 50. The outer ring of the second polarizer 52, like the first polarizer 50, has a plurality of openings sized and positioned to correspond to the diodes of the first illumination source (i.e. every other diode on the first light circuit) such that light emitted from the diodes of the first illumination source passes through the openings unfiltered by the second polarizer 52. Because there are no corresponding openings for the diodes 58 of the second illumination source (i.e. every other diode on the second light circuit) light emitted from second source diodes is polarized by the outer ring of the second polarizer 52. While the switches of the first embodiment 16 and 18 shows only two light sources (i.e. two sets of diodes) three are more sets of diodes are contemplated by the present invention.

Figure 5:
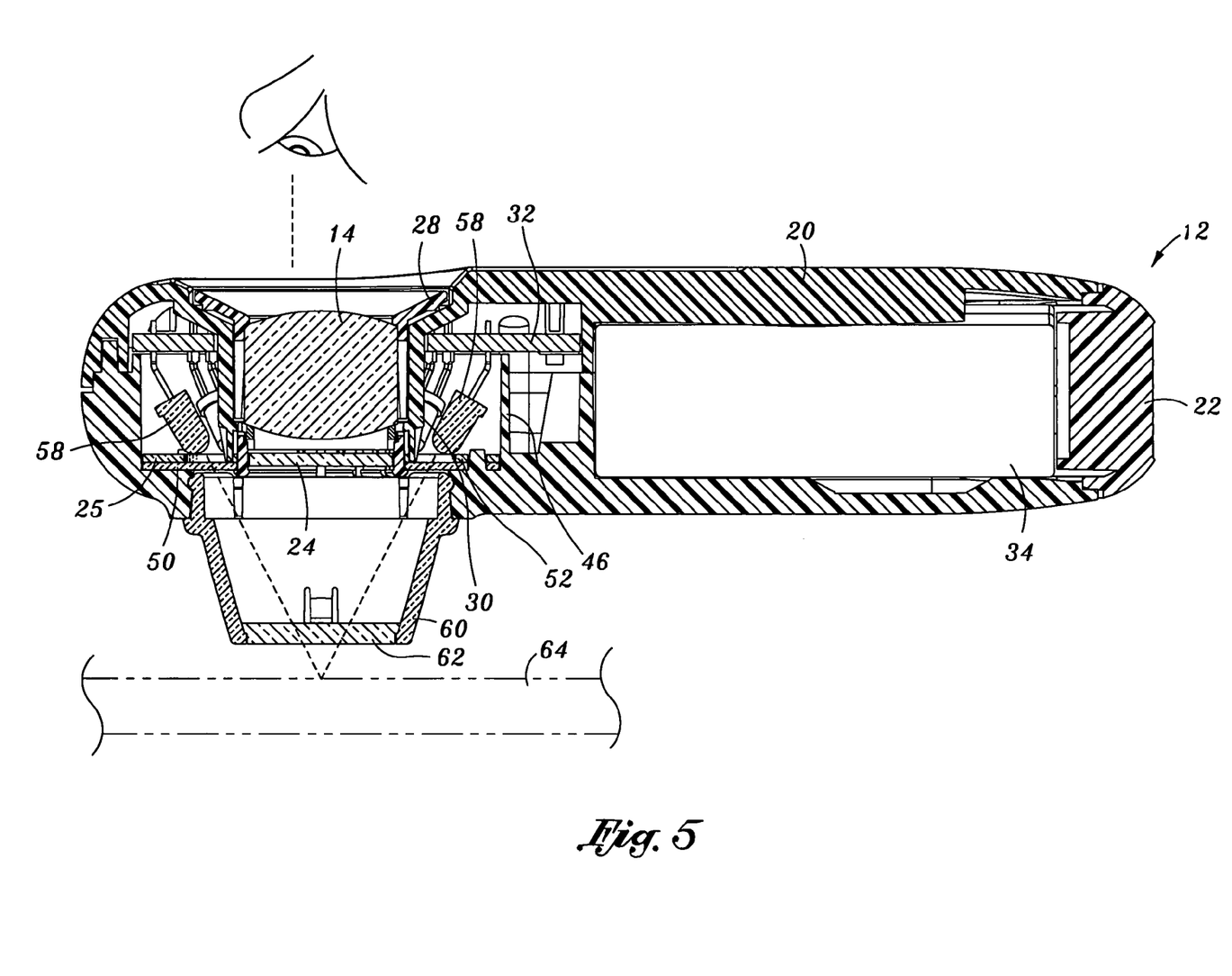
FIG. 5 is a cross-sectional view of the device of a first embodiment of the present invention.

Referring particularly to FIG. 5, there is shown a cross-sectional view of the device 12 of the first embodiment of the present invention. FIG. 5 shows an optional spacer 60 which can engage the viewing portal of the housing 20. The spacer includes glass 62 to provide a transparent barrier. The spacer can aid in achieving the optimal viewing distance between the device 12 and the skin 64. Also, the spacer 60 can prevent contamination of the lens 14 during examination.

FIG. 5 illustrates the angle of mounting of the LEDs 58 upon the PCB 32. The light from the LEDs 58 is angled to concentrate the light onto a focused area are represented by the angled lines shown in phantom. The light from the LEDs 58 is focused into a smaller area, so as to increase the brightness of the LEDs. All of the LEDs 58 in the circle are pointed toward the central area of the region of interest, so as to increase multifold the amount of light directed into the region. It is additionally contemplated by the present invention that some of the LEDs may be directed slightly off center to enlarge the viewing field and to make for uniform lighting.

Figure 6:
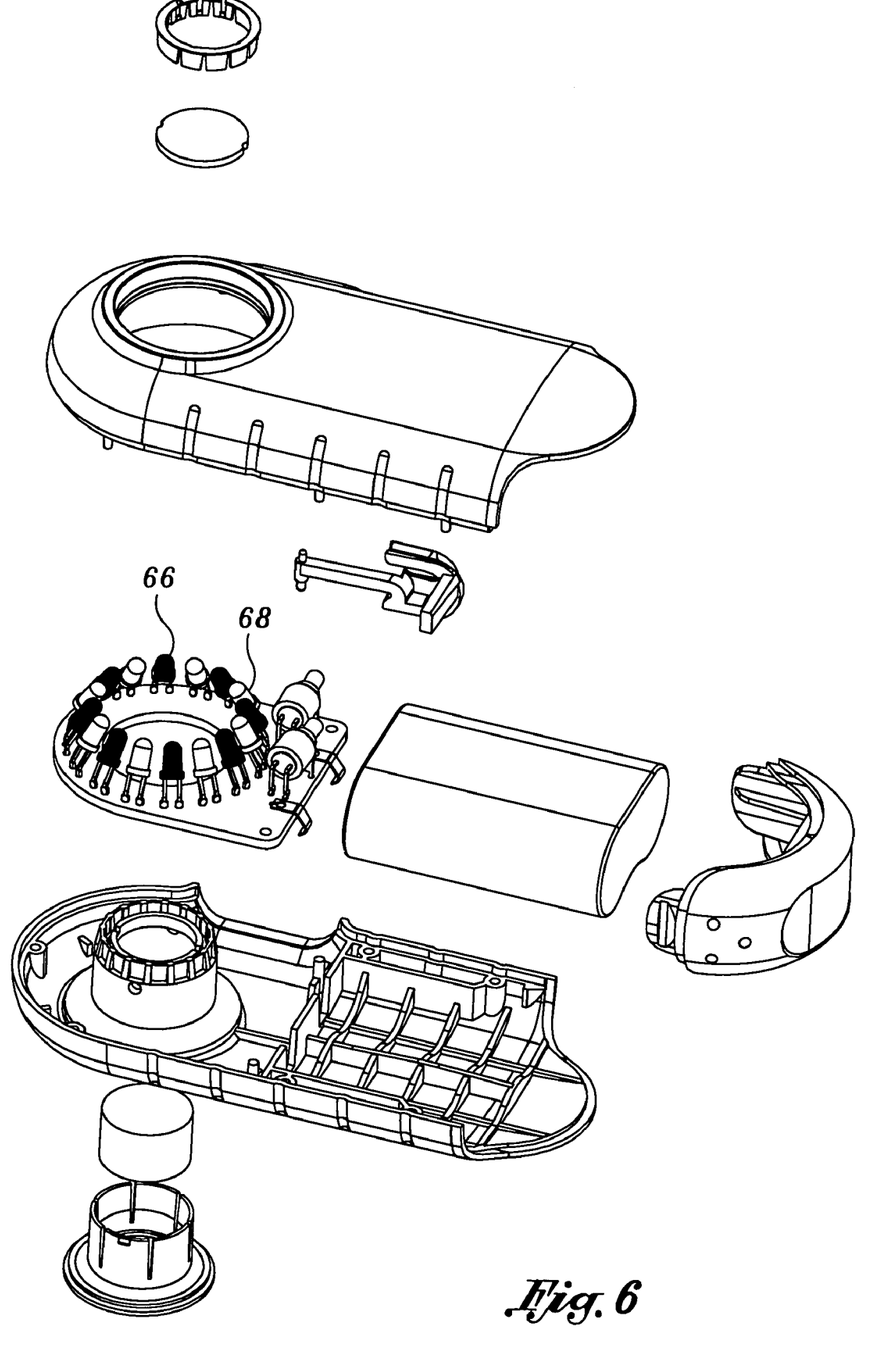
FIG. 6 is and exploded bottom view of a second embodiment of the present invention.
Figure 7:
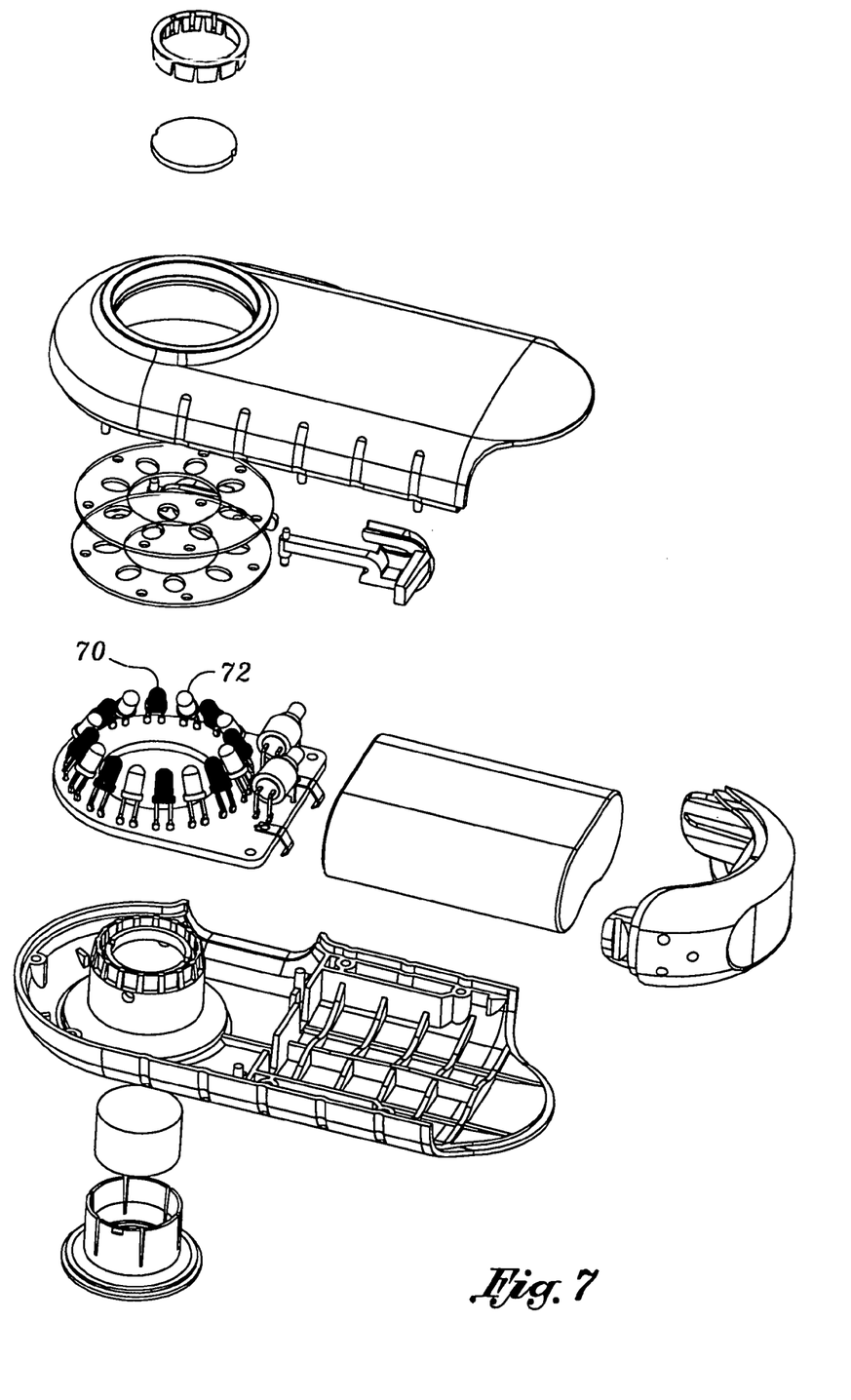
FIG. 7 is and exploded bottom view of a third embodiment of the present invention.

FIG. 6 is a bottom exploded view of a second embodiment of the present invention. The assembly and structure of the device shown in FIG. 6 is identical to that shown in FIGS. 1–5 of the first embodiment of the present invention (and thus the description is not repeated herein), except that the device shown in FIG. 6 does not include two annular filters 50 and 52 and the LEDs 66 and 68 are of different colors. Preferably, the even diodes 66 are of a particular green wavelength and odd diodes 68 are white diodes. The colored LEDs may be different LEDs available at the time such as 370 nm UV, 470 nm blue, 500 nm aqua, 525 nm green, 570 nm orange, 630 nm red, etc. The combination of different colors will provide different imaging capabilities. As an example, the blue light is more absorbed in skin pigmentation and therefore better visualization of pigmentation is achieved with the blue light. Similarly, the green light is more absorbed by the blood and so it is better for visualizing blood vessels. Some compounds also fluoresce at different wavelength light. An example of this is the multiple fluorescence compounds used in research and medicine such as fluorescein, which fluoresces green when illuminated with a blue light. While the second embodiment herein shows green and white diodes, it is understood that the second embodiment could employ any desirable combinations of colors. Likewise, while the switch contemplates only two light sources (i.e. two sets of diodes) three are more sets of diodes are contemplated by the present invention, employing multiple combinations of colors.

FIG. 7 is a bottom exploded view of a third embodiment of the present invention. The assembly and structure of the device shown in FIG. 7 is identical to that shown in FIGS. 1–5 of the first embodiment of the present invention (and thus the description is not repeated herein), except that the device shown in FIG. 7 includes LEDs 70 and 72 are of different colors. Preferably, the even diodes 70 are of a particular green wavelength and odd diodes 72 are white diodes. The two annular polarizers provide cross polarization and parallel polarization identical to that described with respect to the first embodiment. While the third embodiment herein contemplates green and white diodes, it is understood that the third embodiment could employ any desirable combinations of colors. Likewise, while the switches may only initiate two light sources (i.e. two sets of diodes), three are more sets of diodes are contemplated by the present invention, employing multiple combinations of colors.

It should be noted and understood that with respect to the embodiments of the present invention, the materials suggested may be modified or substituted to achieve the general overall resultant high efficiency. The substitution of materials or dimensions remains within the spirit and scope of the present invention.

I claim:

1. A dermoscopy epiluminescence device comprising:
a) a generally circular optical lens defining an outer circumference to produce a magnified image of an object to be observed by a viewer;
b) a first illumination source comprising a plurality of luminous diodes spaced about the circumference of said optical lens to direct light upon the object;
c) a second illumination source comprising a plurality of luminous diodes to direct light upon the object wherein each diode is positioned between diodes of the first illumination source about the circumference of the optical lens to form a ring of alternating diodes from said first and second illumination sources;
d) a first polarizer comprising a planar annular ring filter defining a generally circular center opening and an outer ring, said center opening of said annular ring is positioned in corresponding alignment with the circular optical lens to provide an open view of the object through the lens, said outer ring having a plurality of openings sized and positioned to correspond to the diodes of the second illumination source such that light emitted from the diodes of the second illumination source is passed through the openings toward the object and light emitted from the diodes of the first illumination source is polarized by the first polarizer filter;
e) a second polarizer comprising a planar annular ring filter defining a generally circular center opening and an outer ring, said center opening of said annular ring is positioned in corresponding alignment with the circular optical lens to provide an open view of the object through the lens, said outer ring having a plurality of openings sized and positioned to correspond to the diodes of the first illumination source such that light emitted from the diodes of the first illumination source is passed through the openings toward the object and light emitted from the diodes of the second illumination source is polarized by the second polarizer filter; and
f) a viewing polarizer positioned between a viewer and the object to polarize light reflected from the object wherein said viewing polarizer is cross-polarized relative to said first polarized illumination source and is parallel-polarized relative to said second illumination source.

2. The dermoscopy epiluminescence device of claim 1 further comprising a switch having a first mode for initiating the first illumination source, a second mode for initiating the second illumination source and a third mode for initiating said first and second illumination sources simultaneously.

3. The dermoscopy epiluminescence device of claim 1 wherein said first illumination source and said second illumination source have different color wavelengths.

4. The dermoscopy epiluminescence device of claim 1 further comprising a power source to power said first and second illumination sources.

5. The dermoscopy epiluminescence device of claim 4 wherein said power source is a battery.

6. The dermoscopy epiluminescence device of claim 4 wherein said power source is a lithium battery.

7. The dermoscopy epiluminescence device of claim 1 wherein said luminous diodes are white light emitting diodes.

8. The dermoscopy epiluminescence device of claim 1 wherein said luminous diodes are high light output Indium Gallium Nitride light emitting diodes.

9. The dermoscopy epiluminescence device of claim 1 wherein said optical lens is a Hastings Triplet lens.

10. The dermoscopy epiluminescence device of claim 1 wherein said optical lens is a 15 mm diameter Hastings lens with a 10× optical gain.

11. A selective polarization device for producing a polarized view of an object to be observed by a viewer, the device comprising:
a) an optical lens defining an outer circumference;
b) a plurality of first and second luminous diodes being alternately spaced about said outer circumference to form a ring of diodes;
c) a first polarizer comprising an annular ring filter defining a generally circular center opening, an outer ring and a plurality of openings, said center opening corresponding with the optical lens to provide an open view of the object through the lens, said outer ring substantially corresponding to said outer circumference, said plurality of openings being sized and positioned corresponding to said second diodes with light emitted therefrom being transmittable through the openings toward the object and light emitted from said first diodes being polarized by the first polarizer filter;

d) a second polarizer comprising an annular ring filter defining a generally circular center opening, an outer ring and a plurality of openings, said center opening corresponding with the optical lens to provide an open view of the object through the lens, said outer ring substantially corresponding to said outer circumference, said plurality of openings being sized and positioned corresponding to the first diodes with light emitted therefrom being transmittable through the openings toward the object and light emitted from the second diodes being polarized by the second polarizer filter; and e) a viewing polarizer being positioned between said viewer and being cross-polarized relative to said first polarizer and is parallel-polarized relative to said second polarizer.

12. The device of claim 11 wherein said first and second polarizers are each planar rings.

13. The device of claim 11 wherein said first and second polarizers are substantially mated.

14. The device of claim 11 further comprising a switch having a first mode for initiating said first diodes, a second mode for initiating said second diodes and a third mode for initiating said first and second diodes simultaneously.

15. The device of claim 11 wherein said first and second diodes have different color wavelengths.

16. A selective polarization device for producing a polarized view of an object to be observed by a viewer, the device comprising:

a) an optical lens defining an outer circumference;

b) a plurality of first and second luminous diodes being alternately spaced about said outer circumference to form a ring of diodes;

c) first and second annular polarizers being substantially mated and each defining a center opening and an outer ring, said first polarizers including a plurality of first openings and said second polarizer including a plurality of second openings, said center openings each being aligned with said optical lens providing an open view of the object through the lens, said outer rings each substantially corresponding to said outer circumference, said first openings being sized and positioned corresponding to said second diodes with light emitted therefrom being transmitted through the first openings to be polarized by the second polarizer filter, said second openings being sized and positioned corresponding to said first diodes with light emitted therefrom being transmitted through the second openings to be polarized by the first polarizer filter; and d) a viewing polarizer being positioned between said viewer and being cross-polarized relative to said first polarizer and is parallel-polarized relative to said second polarizer.

17. The device of claim 16 wherein said first and second polarizers are each planar rings.

18. The device of claim 16 further comprising a switch having a first mode for initiating said first diodes, a second mode for initiating said second diodes and a third mode for initiating said first and second diodes simultaneously.

19. The device of claim 16 wherein said first and second diodes have different color wavelengths.

20. The device of claim 16 wherein said pluralities of first and second diodes are pointed inwardly with the light emitted therefrom being directed toward said object.

* * * * *